(12) United States Patent
Yamamoto (10) Patent No.: US 8,714,063 B2
(45) Date of Patent: May 6, 2014

(54) CUTTING AND TRANSFERRING APPARATUS AND CUTTING AND TRANSFERRING METHOD

(75) Inventor: Hiroki Yamamoto, Kanonji (JP)

(73) Assignee: Uni-Charm Corporation, Shikokuchuo-Shi, Ehime-Ken (JP)

( * ) Notice: Subject to any disclaimer, the term of this patent is extended or adjusted under 35 U.S.C. 154(b) by 106 days.

(21) Appl. No.: 13/383,885

(22) PCT Filed: Jul. 30, 2010

(86) PCT No.: PCT/JP2010/062938
§ 371 (c)(1),
(2), (4) Date: Jan. 31, 2012

(87) PCT Pub. No.: WO2011/013820
PCT Pub. Date: Feb. 3, 2011

(65) Prior Publication Data
US 2012/0174721 A1    Jul. 12, 2012

(30) Foreign Application Priority Data

Jul. 31, 2009   (JP) .................................. 2009-180197

(51) Int. Cl.
*B26D 7/06* (2006.01)

(52) U.S. Cl.
USPC ..................................... 83/47; 83/78; 83/100

(58) Field of Classification Search
USPC ......... 83/47, 100, 78, 679, 349, 677, 98, 152, 83/343, 331, 332, 345, 346, 169, 824, 117, 83/449, 493, 310, 373, 674, 322, 24, 165, 83/167; 156/265, 362, 364, 540, 541, 542, 156/363
See application file for complete search history.

(56) References Cited

U.S. PATENT DOCUMENTS

| 1,751,562 | A | * | 3/1930 | Stinger | ........................... 83/115 |
| 5,161,442 | A | * | 11/1992 | Rilitz et al. | ...................... 83/117 |
| 5,415,716 | A | * | 5/1995 | Kendall | ........................ 156/256 |
| 5,609,084 | A | * | 3/1997 | Gronbjerg | ....................... 83/100 |

(Continued)

FOREIGN PATENT DOCUMENTS

| EP | 0819505 A1 | 1/1998 |
| EP | 1132325 B1 | 10/2006 |

(Continued)

OTHER PUBLICATIONS

International Search Report and Written Opinion for PCT/JP2010/062938 dated Oct. 26, 2010.

(Continued)

*Primary Examiner* — Ghassem Alie
(74) *Attorney, Agent, or Firm* — Lowe Hauptman & Ham, LLP (57) ABSTRACT

A cutting and transferring apparatus configured to from a second sheet by cutting a continuous body of second sheets and to transfer the second sheet onto a continuous body of topsheet. The cutting and transferring apparatus includes a blade roll having a blade; a bed knife; and a transfer roll configured to transfer the second sheet onto the continuous body of topsheet. The transfer roll receives an edge portion of the continuous body before cutting. The blade and the bed knife cut the continuous body of the second sheets, in a state where the machine direction MD and a vertical direction coincide with each other.

14 Claims, 5 Drawing Sheets

(56) References Cited

U.S. PATENT DOCUMENTS

| | | | |
|---|---|---|---|
| 6,544,375 B1 | 4/2003 | Schmitz | |
| 6,895,845 B2 * | 5/2005 | Snyder | 83/100 |
| 2004/0244551 A1 | 12/2004 | Snyder | |
| 2005/0067093 A1 * | 3/2005 | Goda et al. | 156/265 |
| 2009/0320663 A1 * | 12/2009 | Yamamoto | 83/100 |
| 2012/0234152 A1 * | 9/2012 | Carmichael | 83/677 |

FOREIGN PATENT DOCUMENTS

| | | |
|---|---|---|
| EP | 1864768 B1 | 11/2009 |
| JP | 10218471 A | 8/1998 |
| JP | 2002193440 A | 7/2002 |
| JP | 2002530255 A | 9/2002 |
| JP | 2006016139 A | 1/2006 |
| JP | 2010063716 A | 3/2010 |

OTHER PUBLICATIONS

Extended European Search Report dated Jun. 12, 2013 corresponds to European Patent Application No. 10804566.7.

Office Action issued Nov. 20, 2013, corresponds to Eurasian patent application No. 201200201.

Office Action mailed Dec. 4, 2013, corresponds to Chinese patent application No. 201080033968.4.

* cited by examiner

CUTTING AND TRANSFERRING APPARATUS AND CUTTING AND TRANSFERRING METHOD

RELATED APPLICATIONS

The present application is a National Phase of International Application Number PCT/JP2010/062938, filed Jul. 30, 2010 and claims priority from Japanese Application Number 2009-180197, filed Jul. 31, 2009.

TECHNICAL FIELD

The present invention relates to a cutting and transferring apparatus as well as a cutting and transferring method for cutting a first continuous body of second sheets or the like in a cross direction to form a strip-shaped first sheet, and transferring the first sheet thus formed onto a second continuous body of topsheets or the like.

BACKGROUND ART

An absorbent article such as a disposable pants-type diaper is formed of multiple sheets, including a liquid-permeable topsheet or second sheet, which is permeable to liquid, a liquid-impermeable waterproof sheet, and a backsheet; and an absorber. In the manufacturing processes of such absorbent articles, a cutting and transferring apparatus is used to form a strip-shaped sheet by cutting a continuous body of sheets substantially horizontally transported, and to dispose (referred to as "transfer") the strip-shaped sheet thus cut onto another sheet (see, for example, Patent Document 1).

The cutting and transferring apparatus includes: a blade roll which is configured to rotate along a machine direction; and a transfer roll which faces the blade roll with a continuous body of second sheets conveyed substantially horizontally, and is configured to rotate along the machine direction. The blade roll has a blade protruding from an outer peripheral surface of the blade roll. The transfer roll has an anvil protruding from an outer peripheral surface of the transfer roll and being configured to come into contact with the blade.

The blade roll and the transfer roll rotate at circumferential speeds which are substantially the same as each other and are faster than a conveyance speed of the second-sheet continuous body conveyed in the machine direction (MD) along the flow of the manufacturing processes. With this configuration, when the second-sheet continuous body is pinched between the blade of the blade roll and the anvil of the transfer roll, the second-sheet continuous body is pulled in the machine direction, and is cut (press-cut) along a cross direction (CD) which is orthogonal to the machine direction. The strip-shaped second sheet thus formed by the cutting is disposed on a top sheet continuous body.

In the press cutting, if the thickness of a continuous body to be cut is increased, there arise a problem of coarsening the cut surface and a problem of difficulty in cutting, in general. In this regard, there has been a demand for a cutting method capable of securely cutting a continuous body even if the thickness of the continuous body is increased. As a method for cutting a continuous body conveyed substantially horizontally, there is shear cutting besides the press cutting.

The shear cutting is performed as follows. A continuous body is fed into between a bed knife and a blade roll. The bed knife is fixed in parallel with and along the entire width of the continuous body in the cross direction, and the blade roll has a blade formed in an outer peripheral surface of the blade roll. Then, the blade is pressed against the bed knife with the continuous body interposed therebetween. Subsequently, the blade is rotated in a direction crossing the plane (surface) of the continuous body to move across the continuous body, thereby cutting the continuous body existing between the blade and the bed knife.

However, it is difficult to employ the shear cutting in the cutting and transferring apparatus described in Patent Literature 1. In the shear cutting, it is impossible to keep holding the continuous body from immediately before the cutting of the continuous body to immediately after the cutting, unlike the press cutting described in Patent Literature 1.

For this reason, what is required is a mechanism (for example, a transfer roll) which is disposed downstream of the bed knife in the machine direction, and which is configured to receive a cut strip-shaped sheet and send to the downstream side as well as to receive the leading edge portion of the continuous body having the cut surface. However, since the receiving mechanism cannot be disposed on the trajectory of the blade near the bed knife, a space is inevitably formed between the bed knife and the receiving mechanism disposed downstream of the bed knife.

A mechanism to convey the continuous body while supporting the leading edge portion of the continuous body cannot be provided between the bed knife and the receiving mechanism. For this reason, the conveyance of the continuous body inevitably depends on the rigidity of the continuous body until the leading edge portion of the continuous body is received by the receiving mechanism.

However, the second-sheet continuous body used in Patent Literature 1 is formed of a soft material. For this reason, it can be considered that the twisting or riding up of the continuous body, that is, defects such as crease and bending are likely to occur before the leading edge portion of the cut continuous body reaches the receiving mechanism.

PRIOR ART DOCUMENT

Patent Document

[Patent Document 1] Japanese Patent Application Publication No. Hei 10-218471 (pp. 4 to 6, FIG. 1)

SUMMARY OF INVENTION

A cutting and transferring apparatus according to first aspect configured to cut a first continuous body of first sheets for absorbent articles in a cross direction orthogonal to a machine direction along a flow of manufacturing processes of the absorbent articles, thereby forming the first sheet, and to transfer the first sheet thus formed onto a second continuous body of second sheets for the absorbent articles. The cutting and transferring apparatus includes: a blade roll being disposed on one side of the first continuous body and having a blade protruding from an outer peripheral surface of the blade roll; a bed knife disposed on the other side of the first continuous body and fixed to face the blade roll with the first continuous body interposed therebetween; and a transfer mechanism disposed downstream of the blade roll and the bed knife in the machine direction, and configured to transfer the first sheet onto the second continuous body, the first sheet being cut by the blade and the bed knife pinching the first continuous body. The transfer mechanism at least receives an edge portion of the first continuous body on a downstream side in the machine direction before the first continuous body is cut. The blade and the bed knife cut the first continuous body guided into between the blade and the bed knife, in a state where the machine direction and a vertical direction coincide with each other.

BRIEF DESCRIPTION OF DRAWINGS

FIG. 4 (a) is a side view showing the cutting and transferring apparatus 100 according to the embodiment at the time of sheet cutting. FIG. 4 (b) is a side view showing the cutting and transferring apparatus 100 according to the embodiment at the time of sheet pressing.

DESCRIPTION OF EMBODIMENTS

Next, embodiments of a cutting and transferring apparatus and a cutting and transferring method according to the present invention will be described with reference to the drawings. Note that, in the following description of the drawings, same or similar reference signs denote same or similar elements and portions. In addition, it should be noted that the drawings are schematic and ratios of dimensions and the like are different from actual ones.

Therefore, specific dimensions and the like should be determined in consideration of the following description. Moreover, the drawings also include portions having different dimensional relationships and ratios from each other.

Figure 1:
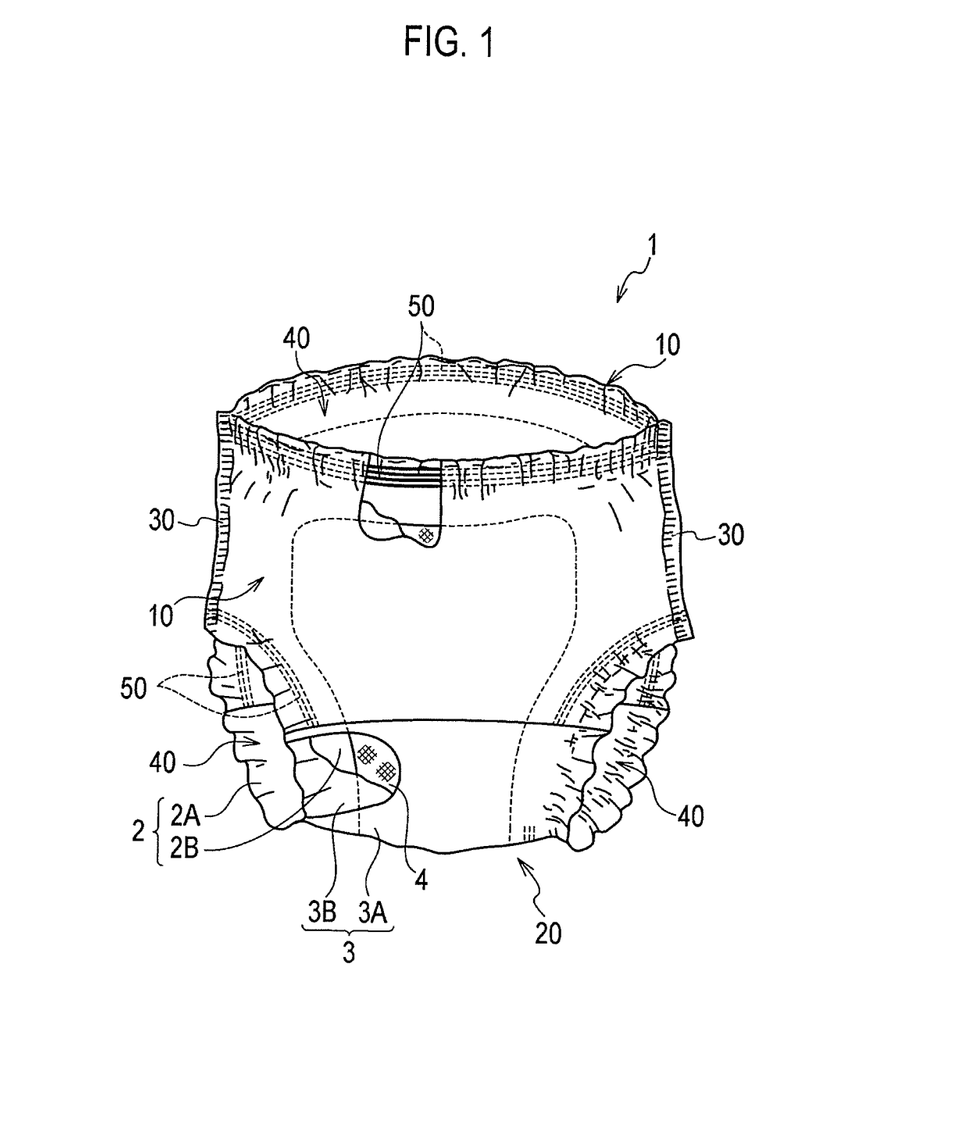
FIG. 1 is a perspective view showing an absorbent article 1 according to an embodiment of the present invention.

First, a configuration of an absorbent article 1 formed by using the cutting and transferring apparatus according to the embodiment will be described with reference to the drawings. FIG. 1 is a perspective view showing the absorbent article 1 according to the embodiment.

In the embodiment, the absorbent article 1 is a disposable pants-type diaper. As shown in FIG. 1, the absorbent article 1 is formed generally of a topsheet 2, a backsheet 3, and an absorber 4.

The topsheet 2 is provided on the innermost side of the absorbent article 1, which comes into contact with the skin of the wearer. The topsheet 2 is formed of a topsheet 2A, which comes into contact with the skin of the wearer, and a second sheet 2B bonded to the topsheet 2A on the absorber 4 side. It should be noted that a liquid-permeable sheet, such as a nonwoven fabric or a perforated plastic film, or the like, is used for the topsheet 2.

The backsheet 3 is provided on the outermost side of the absorbent article 1 (on the side farthest away from the wearer). The backsheet 3 is formed of a backsheet 3A, which is provided on the outermost side of the absorbent article 1, and a waterproof sheet 3B bonded to the backsheet 3A on the absorber 4 side. It should be noted that a nonwoven fabric or the like is used for the backsheet 3A, and a liquid-impermeable sheet or the like is used for the waterproof sheet 3B.

The absorber 4 is provided between the topsheet 2 (the second sheet 2B) and the backsheet 3 (the waterproof sheet 3B), and absorbs excretion from the wearer. The absorber 4 is made of a mixture of a comminuted wood pulp and superabsorbent polymer particles, or the like.

The absorbent article 1 is formed of waistline portions 10 (a front waistline portion and a back waistline portion) to be fitted to the waist of the wearer, and a crotch portion 20 to be fitted to the crotch of the wearer. It should be noted that the waistline portions 10 are joined together by joint portions 30 on the lateral side portions of the waist of the wearer.

The absorbent article 1 is provided with multiple opening portions 40 (a waist opening portion and leg-surrounding opening portions). A gather 50 formed using a rubber cord is provided at the peripheral edge of each of the multiple opening portions 40.

Figure 2:
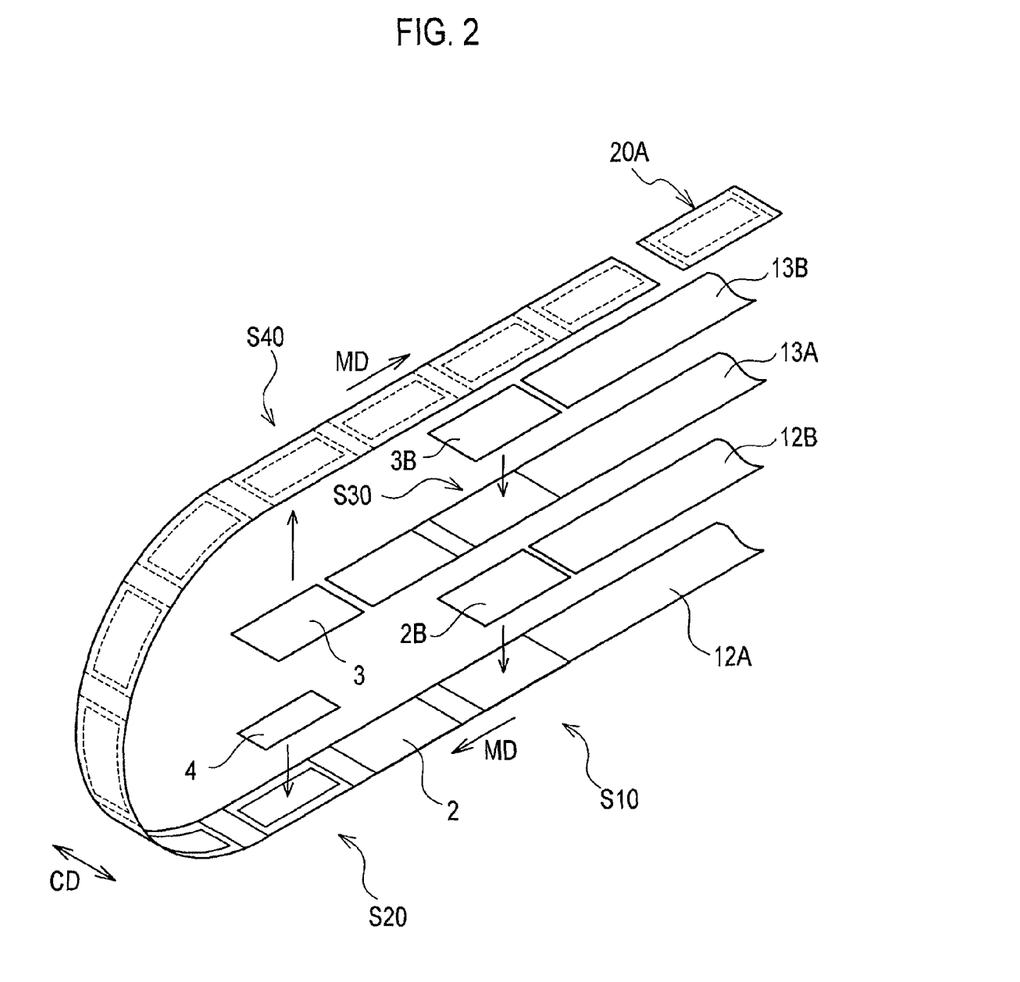
FIG. 2 is a diagram for explaining part of a method for manufacturing a crotch member according to the embodiment.

Next, a cutting and transferring method according to the embodiment will be described with reference to the drawings. FIG. 2 is a diagram for explaining part of the cutting and transferring method according to the embodiment. It should be noted that the cutting and transferring method according to the embodiment will be described by taking a crotch member manufacturing method for manufacturing a crotch member 20A to be processed into the above-described crotch portion 20 as an example.

As shown in FIG. 2, the crotch member manufacturing method includes, at least, a second sheet transfer step S10, a absorber transfer step S20, a waterproof sheet transfer step S30, and a backsheet transfer step S40.

In the second sheet transfer step S10, a second-sheet continuous body 12B in which the second sheets 2B are continuously connected to one another (see FIG. 3) is cut by a cutting and transferring apparatus 100, which will be described later, along a cross direction CD orthogonal to a machine direction MD along the flow of the manufacturing processes of the absorbent article 1. In this way, the strip-shaped second sheet 2B used for the individual absorbent article 1 is formed. Moreover, the second sheet 2B formed by the cutting and transferring apparatus 100 is transferred, at predetermined intervals, onto a topsheet continuous body 12A in which the topsheets 2A are continuously connected to one another.

In the absorber transfer step S20, the absorber 4 formed of a mixture of a comminuted wood pulp and superabsorbent polymer particles, or the like is transferred, at predetermined intervals, onto the topsheet continuous body 12A with the second sheet 2B stacked thereon.

In the waterproof sheet transfer step S30, a waterproof-sheet continuous body 13B in which the waterproof sheet 3B are continuously connected to one another is cut along the cross direction CD by the cutting and transferring apparatus 100, which will be described later. In this way, the strip-shaped waterproof sheet 3B used for the individual absorbent article 1 is formed. Moreover, the waterproof sheet 3B formed by the cutting and transferring apparatus 100 is transferred, at predetermined intervals, onto a backsheet continuous body 13A in which the backsheets 3A are continuously connected to one another.

In the backsheet transfer step S40, the backsheet continuous body 13A with the waterproof sheet 3B stacked thereon is cut along the cross direction CD to form the backsheet 3. Then, the backsheet 3 is transferred, at predetermined intervals, onto the topsheet continuous body 12A with the second sheet 2B and the absorber 4 stacked thereon. After that, the topsheet continuous body 12A with the second sheet 2B, the backsheet 3, and the absorber 4 stacked thereon is cut along the cross direction CD to form the above-described crotch member 20A.

The crotch member 20A formed by the above-described crotch member manufacturing method is joined between a pair of waistline members corresponding to the waistline portions 10, so that the above-described absorbent article 1 is manufactured.

Figure 3:
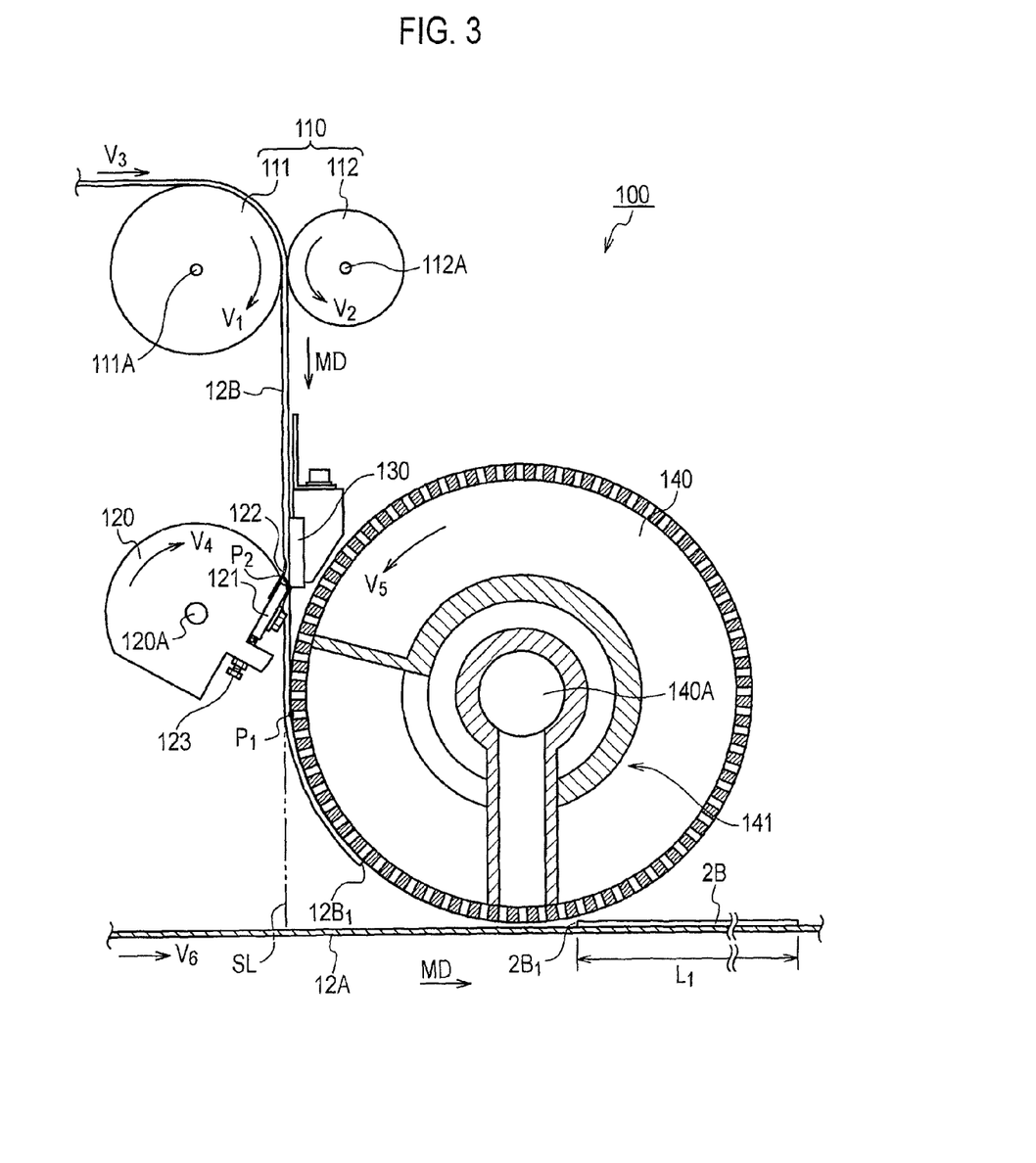
FIG. 3 is a side view showing a cutting and transferring apparatus 100 according to the embodiment.

Next, the configuration of the cutting and transferring apparatus 100 according to the embodiment will be described with reference to the drawings. FIG. 3 is a side view (view in the roll axis direction) showing the cutting and transferring apparatus 100 according to the embodiment. It should be noted that the description will be given herein by taking as an example a case where the cutting and transferring apparatus 100 is used in the second sheet transfer step S10 though the cutting and transferring apparatus 100 is used in the second sheet transfer step S10 and the waterproof sheet transfer step S30 as described above.

As shown in FIG. 3, the cutting and transferring apparatus 100 forms the strip-shaped second sheet 2B by cutting the second-sheet continuous body 12B along the cross direction CD, and transfers the second sheet 2B thus formed onto the topsheet continuous body 12A. The cutting and transferring apparatus 100 includes guide rolls 110 (a guide mechanism), a blade roll 120, a bed knife 130, and a transfer roll 140 (a transfer mechanism).

The guide rolls 110 are disposed upstream of the blade roll 120 and the bed knife 130 in the machine direction MD. The guide rolls 110 guide the second-sheet continuous body 12B into between the blade roll 120 and the bed knife 130 while bringing the machine direction MD into coincidence with the vertical direction. The guide rolls 110 are formed of a first guide roll 111 and a second guide roll 112.

The first guide roll 111 is disposed on one side (the left-hand side in the drawing) of the second-sheet continuous body 12B. The first guide roll 111 rotates along the machine direction MD about a shaft center 111A parallel to a shaft center 120A of the blade roll 120. On the other hand, the second guide roll 112 is disposed on the opposite side (the right-hand side in the drawing) of the second-sheet continuous body 12B. The second guide roll 112 rotates along the machine direction MD about a shaft center 112A parallel to the shaft center 120A of the blade roll 120.

The circumferential speed V1 of the first guide roll 111 and the circumferential speed V2 of the second guide roll 112 are substantially equal to the conveyance speed V3 of the second-sheet continuous body 12B to be guided into between the blade roll 120 and the bed knife 130.

The blade roll 120 is disposed downstream of the guide rolls 110 in the machine direction MD. In addition, the blade roll 120 is disposed on the one side (the left-hand side in the drawing) of the second-sheet continuous body 12B. Moreover, the blade roll 120 is arranged in such a manner that the tangent line of the blade roll 120 coincides with the machine direction MD. The blade roll 120 rotates along the machine direction MD about the shaft center 120A.

The circumferential speed V4 of the blade roll 120 is substantially equal to the circumferential speed V5 of the transfer roll 140, or slower than the circumferential speed V5 of the transfer roll 140. In addition, the circumferential speed V4 of the blade roll 120 is faster than the conveyance speed V3 of the second-sheet continuous body 12B, that is, the circumferential speed V1 of the first guide roll 111 and the circumferential speed V2 of the second guide roll 112.

The blade roll 120 as describe above is formed of a variable-speed roll configured so that the circumferential speed V4 of the blade roll 120 at the time of cutting the second-sheet continuous body 12B is adjustable between the conveyance speed V3 of the second-sheet continuous body 12B and the circumferential speed V5 of the transfer roll 140.

The circumferential speed V4 of the blade roll 120 is varied by a mechanism (not shown) such as a mechanical cam, an electronic cam, or a servo motor whose circumferential speed is controllable. Of the blade roll 120, at least one of a circumferential speed VA and a circumferential speed VB is varied (see FIGS. 4A and 4B). Here, the circumferential speed VA is a circumferential speed of the blade roll 120 at the time of coming into contact with the second-sheet continuous body 12B, and the circumferential speed VB is a circumferential speed of the blade roll 120 for a time period from when the blade roll 120 comes into contact with the second-sheet continuous body 12B to when the blade roll 120 comes into contact with the second-sheet continuous body 12B.

The blade roll 120 configured as described above has a blade 121 and a pressing portion 122. The blade 121 protrudes from an outer peripheral surface of the blade roll 120 outward in a radial direction of the blade roll 120. The blade 121 is fixed onto a planar flat surface portion 12B formed in the blade roll 120, with a fixing member 123, such as a screw. The blade 121 comes into contact with the bed knife 130 at a predetermined cycle, in other words, in conformity with the length L1 of the second sheet 2B in the machine direction MD.

The pressing portion 122 is fixed between the flat surface portion 120B and the blade 121 in such a manner as to be adjacent to a rear side of the blade 121 in the rotational direction of the blade roll 120. The pressing portion 122 is configured to come into contact with the bed knife 130 with the second-sheet continuous body 12B interposed therebetween. The pressing portion 122 configured to press the second-sheet continuous body 12B against the bed knife 130.

The pressing portion 122 protrudes from the outer peripheral surface of the blade roll 120 further than the blade 121. For example, the pressing portion 122 has such a length as to be capable of pressing the second-sheet continuous body 12B against the bed knife 130. The pressing portion 122 is formed of a plate-shaped member made of an elastic material (for example, a rubber belt material). The pressing portion 122 keeps pressing the second-sheet continuous body 12B against the bed knife 130 from a time before the blade 121 and the bed knife 130 come into contact with each other until the second-sheet continuous body 12B is cut and the blade 121 is separated from the bed knife 130.

The bed knife 130 is disposed downstream of the guide rolls 110 in the machine direction MD. In addition, the bed knife 130 is disposed on the opposite side (the right-hand side in the drawing) of the second-sheet continuous body 12B. The bed knife 130 is fixed in such a manner as to face the blade roll 120 with the second-sheet continuous body 12B interposed therebetween.

It should be noted that the above-described blade 121 and bed knife 130 cut the second-sheet continuous body 12B guided into between the blade roll 120 and the bed knife 130 by the guide rolls 110 in a state where the machine direction MD and the vertical direction coincide with each other.

The blade 121 rotates in conjunction with the rotation of the blade roll 120 with respect to the fixed bed knife 130. Thus, the blade 121 cuts the second-sheet continuous body 12B by pinching the second-sheet continuous body 12B with the bed knife 130 in such a way as to move across the second-sheet continuous body 12B (so-called shear cutting).

The transfer roll 140 is disposed downstream of the blade roll 120 and the bed knife 130 in the machine direction MD. The transfer roll 140 is arranged to face the blade roll 120 with the second-sheet continuous body 12B interposed therebetween. In addition, the transfer roll 140 is arranged in such a manner that the tangent line of the transfer roll 140 coincides with the machine direction MD. The transfer roll 140 is configured to transfer the second sheet 2B onto the topsheet continuous body 12A, the second sheet 2B being cut out by the blade 121 and the bed knife 130 pinching the second-sheet continuous body 12B.

The transfer roll 140 is configured to rotate along the machine direction MD about a shaft center 140A parallel to the shaft center 120A of the blade roll 120. The circumferential speed V5 of the transfer roll 140 is faster than the conveyance speed V3 of the transfer roll 140, and also, substantially equal to the conveyance speed V6 of the topsheet continuous body 12A, or slower than the conveyance speed V6 of the topsheet continuous body 12A.

The transfer roll 140 includes a suction mechanism 141 configured to suck the second sheet 2B onto the outer peripheral surface of the transfer roll 140 until the transfer roll 140 completes the transfer of the second sheet 2B onto the topsheet continuous body 12A. Note that the configuration of the suction mechanism 141 is a known technique, and thus is not described herein).

Figure 4:
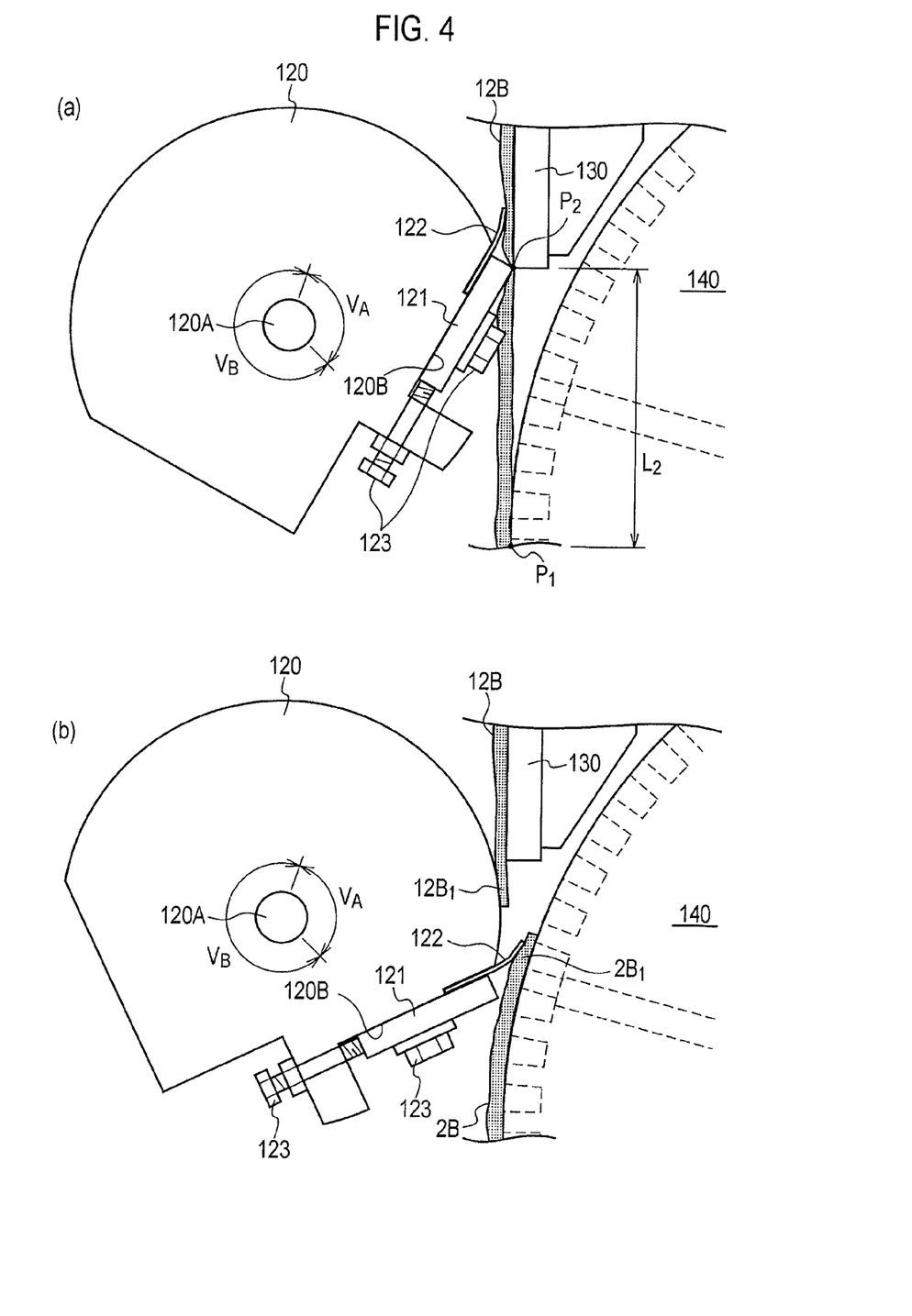

The transfer roll 140 configured as describe above directly receives an edge portion 12B1 (leading edge portion) of the second-sheet continuous body 12B on the downstream side in the machine direction MD before the second-sheet continuous body 12B is cut. To put it differently, a distance L2 between a contact point P1 of the blade 121 of the blade roll 120 and a contact point P2 of the transfer roll 140 on an imaginary line SL drawn in the vertical direction (see FIG. 4 (a)) is not larger than a length L1 of the second sheet 2B in the machine direction MD (see FIG. 3).

Next, the operation of the above-described cutting and transferring apparatus 100 will be described with reference to FIG. 3 as well as FIGS. 4A and 4B. It should be noted that FIG. 4 (a) is a side view showing the cutting and transferring apparatus 100 according to the embodiment at the time of sheet cutting, and FIG. 4 (b) is a side view showing the cutting and transferring apparatus 100 according to the embodiment at the time of sheet pressing.

First, as shown in FIG. 3, the cutting and transferring apparatus 100 guides the second-sheet continuous body 12B into between the blade roll 120 and the bed knife 130 by the guide rolls 110. At this time, the circumferential speed V5 of the transfer roll 140 is faster than the conveyance speed V3 of the second-sheet continuous body 12B. For this reason, the edge portion 12B1 of the second-sheet continuous body 12B on the downstream side in the machine direction MD is sucked onto the outer peripheral surface of the transfer roll 140 by the suction mechanism 141 while sliding on the outer peripheral surface of the transfer roll 140. In other words, the transfer roll 140 receives the edge portion 12B1 of the second-sheet continuous body 12B before the second-sheet continuous body 12B is cut.

Secondly, as shown in FIG. 4 (a), the cutting and transferring apparatus 100 uses the blade 121 rotating in conjunction with the rotation of the blade roll 120 with respect to the fixed bed knife 130, and thereby cuts the second-sheet continuous body 12B by pinching the second-sheet continuous body 12B between the bed knife 130 and the blade 121 in such a manner as to cause the blade 121 to move across the second-sheet continuous body 12B (so-called shear cutting). In this way, the cutting and transferring apparatus 100 forms the second sheet 2B.

In this event, the pressing portion 122 keeps pressing the edge portion 12B1 of the second-sheet continuous body 12B against the bed knife 130 from a time before the blade 121 and the bed knife 130 come into contact with each other until the second-sheet continuous body 12B is cut and the blade 121 is separated from the bed knife 130.

Thirdly, as shown in FIG. 4 (b), the cutting and transferring apparatus 100 presses an upstream edge portion 2B1 of the second sheet 2B in the machine direction MD against the outer peripheral surface of the transfer roll 140 by the pressing portion 122 immediately after the second-sheet continuous body 12B is cut and the blade 121 is separated from the bed knife 130.

Specifically, the pressing portion 122 presses the edge portion 2B1 of the second sheet 2B against the outer peripheral surface of the transfer roll 140 because the circumferential speed V4 of the blade roll 120 is faster than the conveyance speed V3 of the second-sheet continuous body 12B.

Fourthly, as shown in FIG. 3, the cutting and transferring apparatus 100 transfers the second sheet 2B onto the topsheet continuous body 12A by the transfer roll 140. Specifically, the transfer roll 140 transfers the second sheet 2B onto the topsheet continuous body 12A by releasing (for example, blowing air) the suction of the second sheet 2B along the outer peripheral surface of the transfer roll 140, which is performed by the suction mechanism 141, in a state where the second sheet 2B is placed on the topsheet continuous body 12A.

In the embodiment described above, the blade 121, which rotates in conjunction with the rotation of the blade roll 120 with respect to the fixed bed knife 130, cuts the second-sheet continuous body 12B by pinching the second-sheet continuous body 12B with the bed knife 130 in such a way as to move across the second-sheet continuous body 12B (so-called shear cutting). According to this configuration, even if the thickness of the second sheet 2B is increased, the second sheet 2B can be cut more securely than a case where the second-sheet continuous body 12B is ripped in the machine direction MD while being pressed (press cutting).

In addition, the transfer roll 140 at least receives the edge portion 12B1 of the second-sheet continuous body 12B before the second-sheet continuous body 12B is cut. According to this configuration, at the time of cutting the second-sheet continuous body 12B, the second-sheet continuous body 12B is cut in a pulled state. This makes it possible to stabilize the cutting of the second-sheet continuous body 12B and to suppress the coarsening of the cut surface (leading edge portion) of the second-sheet continuous body 12B.

Moreover, the blade roll 120 and the bed knife 130 cut the second-sheet continuous body 12B guided into between the blade roll 120 and the bed knife 130, in a state where the machine direction MD and the vertical direction coincide with each other. According to this configuration, since the edge portion 12B1 of the second-sheet continuous body 12B is set along the vertical direction, the edge portion 12B1 of the second-sheet continuous body 12B can be prevented from entering a space formed between the bed knife 130 and the transfer roll 140. For this reason, the edge portion 12B1 of the second-sheet continuous body 12B is securely passed to the transfer roll 140, and therefore, the twisting or riding up of the second-sheet continuous body 12B can be securely suppressed, that is, occurrences of defects, such as crease and bending, in the second-sheet continuous body 12B can be securely suppressed. Accordingly, the second-sheet continuous body 12B is never cut in a state where any defect has occurred in the second-sheet continuous body 12B, and also the second sheet 2B is never transferred onto the topsheet continuous body 12A in a state where any defect has occurred in the second sheet 2B.

As described above, even if the thickness of the second sheet 2B used for the absorbent article 1 is increased, there is no need to slow down the speed of manufacturing the absorbent article 1, the second sheet 2B can be securely cut, and the second sheet 2B can be transferred with no occurrence of defects such as crease and bending. For this reason, failure in manufacture of the absorbent article 1 can be suppressed.

In the embodiment, the guide rolls 110 guide the second-sheet continuous body 12B into between the blade roll 120 and the bed knife 130 in a state where the machine direction MD and the vertical direction coincide with each other. According to this configuration, since the edge portion 12B1 of the second-sheet continuous body 12B is securely set along the vertical direction, the edge portion 12B1 of the second-sheet continuous body 12B can be more securely prevented from entering a space formed between the bed knife 130 and the transfer roll 140.

In the embodiment, the distance L2 between the contact point P1 of the blade 121 of the blade roll 120 and the contact point P2 of the transfer roll 140 on the imaginary line SL drawn in the vertical direction is not longer than the length L1 of the second sheet 2B in the machine direction MD. It should be noted that, if the distance L2 is larger than the length L1, it is possible that the transfer roll 140 cannot receive the edge portion 12B1 of the second-sheet continuous body 12B successfully, so that a defect such as crease or bending occurs in the edge portion 12B1 of the second-sheet continuous body 12B.

In the embodiment, the pressing portion 122 keeps pressing the edge portion 12B1 of the second-sheet continuous body 12B against the bed knife 130 from a time before the blade 121 and the bed knife 130 come into contact with each other until the second-sheet continuous body 12B is cut and the blade 121 is separated from the bed knife 130. According to this configuration, when the circumferential speed V4 of the blade roll 120 is set to be faster than the conveyance speed V3 of the second-sheet continuous body 12B, the edge portion 12B1 of the second-sheet continuous body 12B can be positioned before the blade 121 and the bed knife 130 come into contact with each other, and also, crease that has occurred in the second-sheet continuous body 12B can be stretched. In addition, it is possible to suppress the rising up of the edge portion 12B1 of the second-sheet continuous body 12B from the bed knife 130 toward the blade 121 because of the movement of the blade 121 at the moment when the blade 121 is separated from the bed knife 130. Accordingly, the edge portion 12B1 of the second-sheet continuous body 12B is stably disposed with respect to the bed knife 130, and the cutting of the second-sheet continuous body 12B is more securely stabilized.

In addition, the pressing portion 122 may be configured to press the edge portion 2B1 of the second sheet 2B against the outer peripheral surface of the transfer roll 140 immediately after the second-sheet continuous body 12B is cut and the blade 121 is separated from the bed knife 130. According to this configuration, the edge portion 2B1 of the second sheet 2B which has not yet been sucked onto the outer peripheral surface of the transfer roll 140 is sucked onto the outer peripheral surface of the transfer roll 140 before hanging down due to the gravity. For this reason, the occurrence of defects such as crease and bending in the edge portion 2B1 of the second sheet 2B can be securely suppressed.

In the embodiment, the pressing portion 122 is formed of a plate-shaped member made of an elastic material, and comes into contact with the bed knife 130 with the second-sheet continuous body 12B interposed therebetween. According to this configuration, even when the pressing portion 122 rotating in conjunction with the rotation of the blade roll 120 comes into contact with the bed knife 130, the pressing portion 122 is deformed. Therefore, the pressing portion 122 can press the edge portion 2B1 of the second sheet 2B against the bed knife 130 without interfering with the rotation of the blade roll 120, and also, can press the edge portion 2B1 of the second sheet 2B toward the outer peripheral surface of the transfer roll 140.

In the embodiment, the blade roll 120 is formed of a variable-speed roll. For example, the blade roll 120 satisfies the relation of VA>VB, where VA represents the circumferential speed of the blade roll 120 at the time of coming into contact with the second-sheet continuous body 12B, and VB represents the circumferential speed of the blade roll 120 for a time period from when the blade roll 120 comes into contact with the second-sheet continuous body 12B to when the blade roll 120 comes into contact with the second-sheet continuous body 12B again. According to this configuration, since the blade roll 120 can rotate at an appropriate speed in accordance with the thickness or material of the second-sheet continuous body 12B, the accuracy of cutting the second-sheet continuous body 12B is improved.

In the embodiment, the first guide roll 111 and the second guide roll 112 rotate along the machine direction MD respectively about the shaft center 111A and the shaft center 112A, thereby guiding the second-sheet continuous body 12B into between the blade roll 120 and the bed knife 130. According to this configuration, the second-sheet continuous body 12B can be securely guided into between the blade roll 120 and the bed knife 130 in a state where the machine direction MD and the vertical direction coincide with each other. Therefore, the cutting and receiving of the second-sheet continuous body 12B are stabilized, so that the occurrence of defects such as crease and bending in the second-sheet continuous body 12B can be more securely suppressed.

In the embodiment, the blade roll 120 and the transfer roll 140 are disposed in such a manner that the respective tangent lines of the blade roll 120 and the transfer roll 140 coincide with the machine direction MD. According to this configuration, the blade roll 120 can more securely cut the second-sheet continuous body 12B, which is conveyed by the guide rolls 110 with the machine direction MD and the vertical direction coinciding with each other. In addition, the transfer roll 140 can more securely receive the second-sheet continuous body 12B, which is conveyed by the guide rolls 110 with the machine direction MD and the vertical direction coinciding with each other. Therefore, the cutting and receiving of the second-sheet continuous body 12B are stabilized, so that the occurrence of defects such as crease and bending in the second-sheet continuous body 12B can be more securely suppressed.

(Modification)

Figure 5:
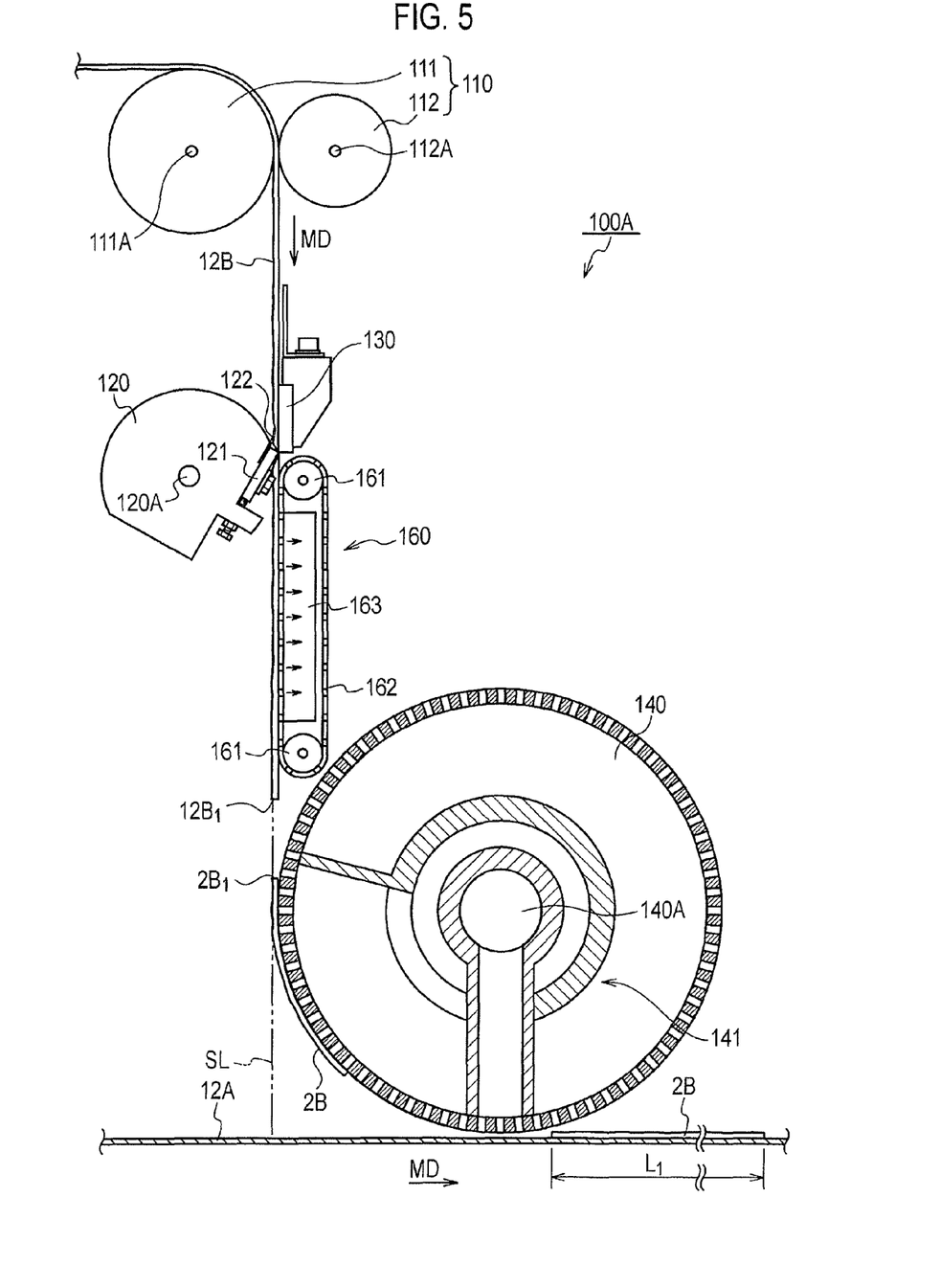
FIG. 5 is a side view showing a cutting and transferring apparatus 100A according to a modification.

Next, a modification of the cutting and transferring apparatus 100 according to the above-described embodiment will be described with reference to the drawings. FIG. 5 is a side view (view in the roll axis direction) showing a cutting and transferring apparatus 100A according to the modification. It should be noted that the same reference numerals denote the same portions as those in the cutting and transferring apparatus 100 according to the above-described embodiment, and portions different from the cutting and transferring apparatus 100 according to the above-described embodiment will be mainly described.

In the above-described embodiment, the transfer roll 140 directly receives the downstream-side edge portion 12B1 of the second-sheet continuous body 12B in the machine direction MD before the second-sheet continuous body 12B is cut. By contrast, in the modification, as shown in FIG. 5, the transfer roll 140 receives the downstream-side edge portion 12B1 of the second-sheet continuous body 12B via a belt conveyor 160.

It should be noted that the belt conveyor 160 is formed of multiple rollers (for example, a roller 161 and an unillustrated drive roller), an endless conveyor belt 162, and a suction mechanism 163 having the same function as that of the suction mechanism 141.

According to the cutting and transferring apparatus 100A of the modification described above, even if the thickness of a sheet, such as the second sheet 2B used for the absorbent article 1, is increased, failure in manufacture of the absorbent article 1 due to defects such as crease and bending occurring in the sheet can be suppressed, in the same manner as that of the operations and effects described in the embodiment.

In particular, when the diameter of the transfer roll 140 is large, or when the length L1 of the second sheet 2B in the machine direction MD is long, the provision of the belt conveyor 160 makes it possible to suppress failure in manufacture of the absorbent article 1 due to defects such as crease and bending occurring in the second sheet 2B can be suppressed.

Other Embodiments

As described above, the details of the present invention have been disclosed by using the embodiments of the present invention. However, it should not be understood that the description and drawings which constitute part of this disclosure limit the present invention. From this disclosure, various alternative embodiments, examples, and operation techniques will be easily found by those skilled in the art.

For example, the embodiment of the present invention may be modified as described below. Specifically, although the absorbent article 1 has been described so far as the disposable pants-type diaper, the absorbent article 1 is not limited to the disposable pants-type diaper, and may be an open-type diaper or a napkin. Note that, needless to say, the configuration of the absorbent article 1 is not limited to that described in the embodiment, and may be set as appropriate for the purpose.

In addition, although the cutting and transferring apparatus 100 has been described as one used in the second sheet transfer step S10, the cutting and transferring apparatus 100 is not limited to this case, may be used in the waterproof sheet transfer step S30, and of course, may be used in any other manufacturing step for the absorbent article 1.

Moreover, the configurations and shapes of the guide rolls 110, the blade roll 120, the bed knife 130, the transfer roll 140 are not limited to those described in the embodiment, and may be set as appropriate for the purpose.

For example, as the transfer mechanism, it is not necessarily to employ the transfer roll 140, and may employ a transfer belt conveyor capable of receiving the second sheet 2B and transferring the second sheet 2B onto the topsheet continuous body 12A instead of the transfer roll 140.

In addition, as the guide mechanism, it is not necessarily to employ the guide rolls 110, but may employ any configuration (for example, a belt conveyor) other than rolls as long as the configuration is capable of guiding the second-sheet continuous body 12B into between the blade roll 120 and the bed knife 130 in a state where the machine direction MD and the vertical direction coincide with each other.

Moreover, the pressing portion 122 does not necessarily need to be formed of an elastic material, and requires only such a configuration as to be capable of pressing the edge portion 2B1 of the second sheet 2B against the outer peripheral surface of the transfer roll 140. Furthermore, the blade roll 120 does not necessarily need to have the pressing portion 122, and it is sufficient for the blade roll 120 not to have the pressing portion 122.

As described above, the present invention naturally includes various embodiments which are not described herein. Accordingly, the technical scope of the present invention should be determined only by the matters to define the invention in the scope of claims regarded as appropriate based on the description.

Note that, the entire content of Japanese Patent Application No. 2009-180197 (filed on Jul. 31, 2009) is incorporated herein by reference.

INDUSTRIAL APPLICABILITY

The aspect of the present invention can provides a cutting and transferring apparatus and a cutting and transferring method capable of securely cutting a sheet such as a second sheet used for an absorbent article even if the thickness of the sheet is increased, and capable of transferring the sheet with no occurrence of defects such as crease and bending.

The invention claimed is:

1. A method of cutting a first continuous body of first sheets for absorbent articles in a cross direction orthogonal to a machine direction along a flow of manufacturing processes of the absorbent articles, thereby forming the first sheet, and transferring the first sheet thus formed onto a second continuous body of second sheets for the absorbent articles, the method comprising:
    forming the first sheet by a blade and a bed knife pinching and cutting the first continuous body, the blade protruding from an outer peripheral surface of a blade roll disposed on one side of the first continuous body, the bed knife disposed on the other side of the first continuous body; and
    transferring the first sheet onto the second continuous body by a transfer mechanism disposed downstream of the blade roll and the bed knife in the machine direction,
    wherein
    the transfer mechanism at least receives an edge portion of the first continuous body on a downstream side in the machine direction before the first continuous body is cut,
    the blade and the bed knife cut the first continuous body guided between the blade and the bed knife, in a state where the machine direction and a vertical direction coincide with each other,
    a pressing portion of the blade roll presses the first continuous body against the bed knife, and
    the pressing portion presses the first sheet against the transfer mechanism after the first continuous body is cut.

2. A cutting and transferring apparatus configured to cut a first continuous body of first sheets for absorbent articles in a cross direction orthogonal to a machine direction along a flow of manufacturing processes of the absorbent articles, thereby forming the first sheet, and to transfer the first sheet thus formed onto a second continuous body of second sheets for the absorbent articles, the cutting and transferring apparatus comprising:
    a blade roll configured to be disposed on one side of the first continuous body and having a blade protruding from an outer peripheral surface of the blade roll;
    a bed knife configured to be disposed on the other side of the first continuous body and fixed to face the blade roll with the first continuous body interposed therebetween; and
    a transfer mechanism disposed downstream of the blade roll and the bed knife in the machine direction, and configured to transfer the first sheet onto the second continuous body,
    wherein
    the blade is configured to cut the first continuous body by pinching the first continuous body with the bed knife to obtain the first sheet, the transfer mechanism is configured to at least receive an edge portion of the first continuous body on a downstream side in the machine direction before the first continuous body is cut, the blade and the bed knife are configured to cut the first continuous body guided between the blade and the bed knife, in a state where the machine direction and a vertical direction coincide with each other, the blade roll further has a pressing portion, the pressing portion is configured to press the first continuous body against the bed knife, and the pressing portion is configured to press the first sheet against the transfer mechanism after the first continuous body is cut.

3. The cutting and transferring apparatus according to claim 2, further comprising a guide mechanism disposed upstream of the blade roll and the bed knife in the machine direction, and configured to guide the first continuous body between the blade and the bed knife in the state where the machine direction and the vertical direction coincide with each other.

4. The cutting and transferring apparatus according to claim 2, wherein the transfer mechanism includes a transfer roll configured to rotate along the machine direction about a shaft center parallel to a shaft center of the blade roll, and a distance between (i) a contact point of the blade with the first continuous body and (ii) a contact point of the transfer roll with the first continuous body on an imaginary line drawn along the vertical direction is not larger than a length of the first sheet in the machine direction.

5. The cutting and transferring apparatus according to claim 4, wherein the pressing portion is located adjacent to a rear side of the blade in a rotational direction of the blade roll, and the pressing portion protrudes from the outer peripheral surface of the blade roll further than the blade.

6. The cutting and transferring apparatus according to claim 5, wherein the pressing portion includes an elastic material.

7. The cutting and transferring apparatus according to claim 4, wherein a tangent line of the transfer roll coincides with the machine direction and the vertical direction.

8. The cutting and transferring apparatus according to claim 4, wherein the blade roll includes a variable-speed roll configured so that a circumferential speed of the blade roll at the time of cutting the first continuous body is adjustable between a circumferential speed of the transfer roll and a conveyance speed of the first continuous body.

9. The cutting and transferring apparatus according to claim 8, wherein the blade roll is configured to have a first circumferential speed at the time of the blade coming into contact with the first continuous body and a second circumferential speed for a time period from when the blade comes into contact with the first continuous body to cut the first continuous body to when the blade comes into contact with the first continuous body to cut the first continuous body again, and the first circumferential speed is greater than the second circumferential speed.

10. The cutting and transferring apparatus according to claim 2, wherein the pressing portion is configured to be in a curved state when pressing the first continuous body against the bed knife and when pressing the first sheet against the transfer mechanism after the first continuous body is cut.

11. The cutting and transferring apparatus according to claim 2, wherein the pressing portion is configured to be elastically deformed when pressing the first continuous body against the bed knife and when pressing the first sheet against the transfer mechanism after the first continuous body is cut.

12. The cutting and transferring apparatus according to claim 2, wherein the pressing portion comprises:

a first end fixed to the blade roll; and a second end that is not directly fixed to the blade roll and is configured to directly press the first continuous body against the bed knife and to directly press the first sheet against the transfer mechanism after the first continuous body is cut.

13. The cutting and transferring apparatus according to claim 12, wherein the pressing portion is a plate.

14. The cutting and transferring apparatus according to claim 2, wherein the pressing portion is configured to press the first sheet against an outer peripheral surface of the transfer mechanism after the first continuous body is cut.

* * * * *